US006210354B1

(12) United States Patent
Ousdal

(10) Patent No.: US 6,210,354 B1
(45) Date of Patent: Apr. 3, 2001

(54) DEVICE FOR A STRETCH CORSET AND A NECK STRETCHER

(76) Inventor: Svein Ousdal, Oftedal, N-4580 Lynodal (NO)

( * ) Notice: Subject to any disclaimer, the term of this patent is extended or adjusted under 35 U.S.C. 154(b) by 0 days.

(21) Appl. No.: 09/238,866

(22) Filed: Jan. 27, 1999

Related U.S. Application Data

(63) Continuation of application No. 08/894,496, filed on Jul. 16, 1997, now Pat. No. 5,916,188.

(30) Foreign Application Priority Data

Jan. 18, 1995 (NO) .................................................... 950179

(51) Int. Cl.[7] ........................................................ A61F 5/00
(52) U.S. Cl. ............................................... 602/36; 602/18
(58) Field of Search ............................... 602/32, 18, 19, 602/33, 36, 38; 128/DIG. 23; 606/240, 241

(56) References Cited

U.S. PATENT DOCUMENTS

| 1,463,081 | * | 7/1923 | Hancock | 128/DIG. 23 X |
| 1,722,205 | * | 7/1929 | Freund | 602/19 |
| 2,886,031 | * | 5/1959 | Robbins | 602/19 |
| 3,413,971 | * | 12/1968 | Evans | 602/32 |
| 4,245,627 | * | 1/1981 | Mignard | 602/19 |
| 4,250,874 | * | 2/1981 | Rude | 602/36 |
| 4,715,362 | * | 12/1987 | Scott | 602/36 |
| 5,462,518 | * | 10/1995 | Hatley et al. | 602/36 |
| 5,916,188 | * | 6/1999 | Ousdal | 602/19 X |

FOREIGN PATENT DOCUMENTS

3438169 A1 * 7/1985 (DE) ...................................... 602/32

* cited by examiner

Primary Examiner—Glenn E. Richmon
Assistant Examiner—Denise Pothier
(74) Attorney, Agent, or Firm—Head, Johnson & Kachigian

(57) ABSTRACT

A device for exerting force between two portions of the human anatomy, such as a back or neck. The device includes an upper brace for attachment to an upper portion of the human anatomy and a lower brace for attachment to a lower portion of the human anatomy. The first and the second fluid containing cylinder, each cylinder having a lower portion and a telescopically extendable upper portion, have attachment means thereon and extend generally in a longitudinal direction of a patient. The first cylinder upper portion is attached to the upper brace, the first cylinder lower portion is attached to the lower brace. The second cylinder upper portion is attached to the upper brace and the second cylinder lower portion is attached to the lower brace. The first and second cylinders are positioned on opposite sides of the human anatomy with the fluid within the cylinders being compressive and under compression providing a constant force urging the upper brace away from the lower brace. The upper brace has an articulation mechanism for providing mobility to the patient.

3 Claims, 5 Drawing Sheets

DEVICE FOR A STRETCH CORSET AND A NECK STRETCHER

This is continuation application of Serial No.08/894,496 filed on Jul. 16, 1997, U.S. Pat. No. 5,916,188 which relates to PCT Application No. NO96/00006 which claims priority from Norwegian Patent Application No. 950179 filed on Jan. 18, 1995.

SUMMARY OF THE INVENTION

This invention relates to a device for a stretch corset and a neck stretcher in order to stretch out the spine of a patient in connection with back and/or neck sufferings, and where two opposing belts or the like positioned beneath the arms of the patient and within the hip area, respectively—with neck damages—where opposing yoke on the shoulders and head support become supported against each other by means of adjustable, possibly resilient means at each side of the patient.

In order to reduce a patient's back pains and/or neck pains and, possibly, cure damages in the back and/or the neck, it is known to stretch out the spine of the patient by means of a stretching device fixed to the patient. Such stretch devices where opposing belt or the like positioned below the arms of the patient and within the hip area, respectively upon neck damages—where opposing yoke on the shoulders and head support are supported against each other by means of adjustable, possibly resilient means, e.g. by disposing spiral springs within cylinders, are previously disclosed in U.S. Pat. Nos. 2,886,031, 3,029,810, 3,413,971,4,245,627,4,250,874,4,715,362 and 4,987,885.

The stretch device closest to the present invention is disclosed in U.S. Pat. No. 3,413,971, dealing with a training apparatus in the form of an orthopaedic stretching apparatus which is not designed with a view of being carried permanently by a patient having back and neck sufferings, but can exclusively be used for training purposes. This training apparatus comprises interconnected and, thus, communicating pressure fluid operated piston cylinders. The object of these communicating cylinders is to secure mutually equal tensile strain on each side of back and/or neck.

With a stretch corset and a neck stretcher of the kind with which the present invention deals, it is intended to allow lateral bending of the back, head and neck ofthe patient. A great disadvantage of the other known devices of this kind is that they, to a very high degree, hamper the patient's movements of the spine.

The object of this invention is to provide a device for a stretch corset and neck support, causing that the patient is not hampered in his/her movements of spine/head/neck.

BRIEF DESCRIPTION OF THE DRAWINGS

Two examplary embodiments of the invention are shown in the accompanying drawings, wherein.

DETAILED DESCRIPTION OF THE PREFERRED EMBODIMENTS

Figure 1:
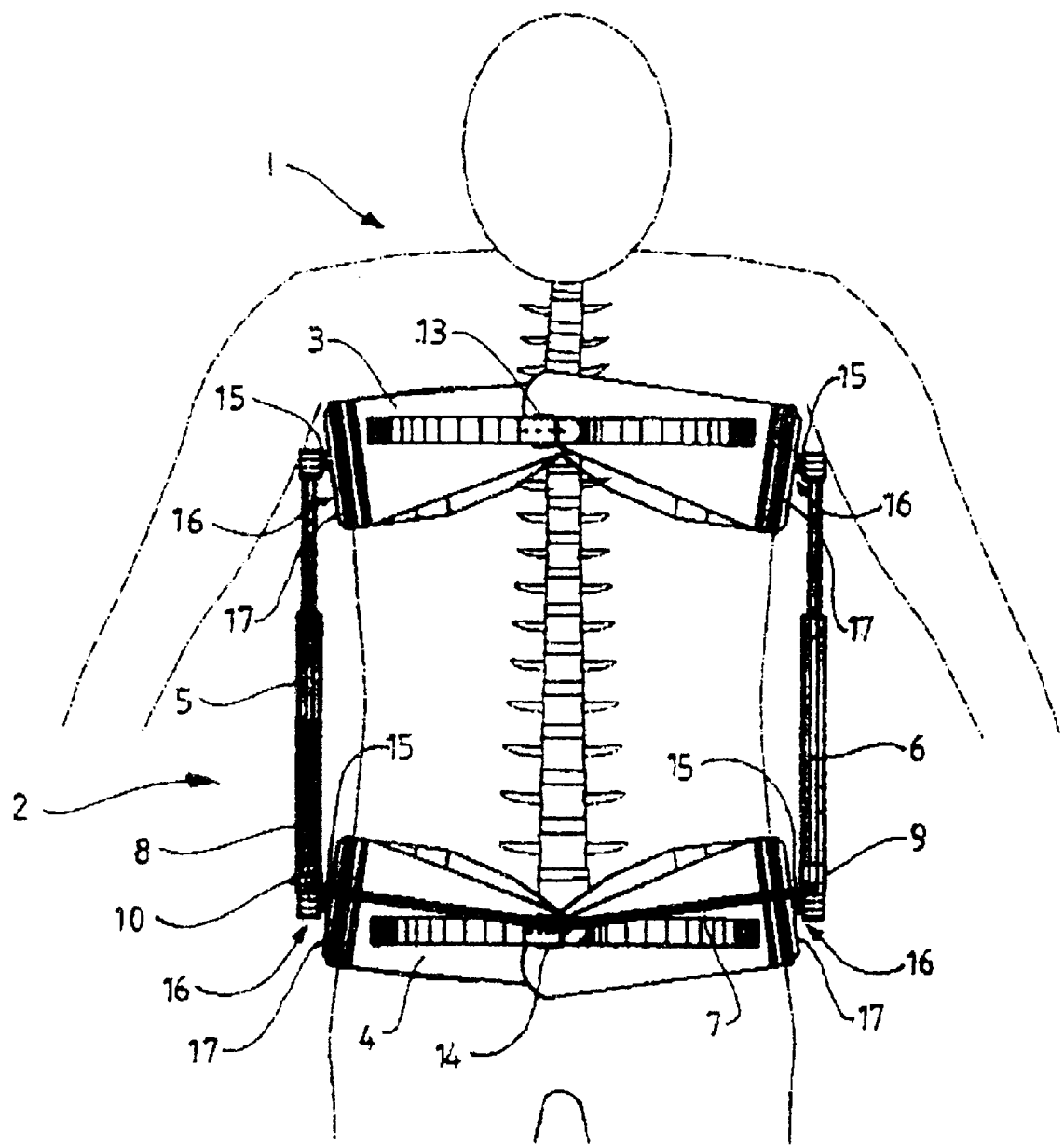
FIG. 1 shows a stretch corset in a front view, fastened on a patient standing in a straight position.
Figure 2:
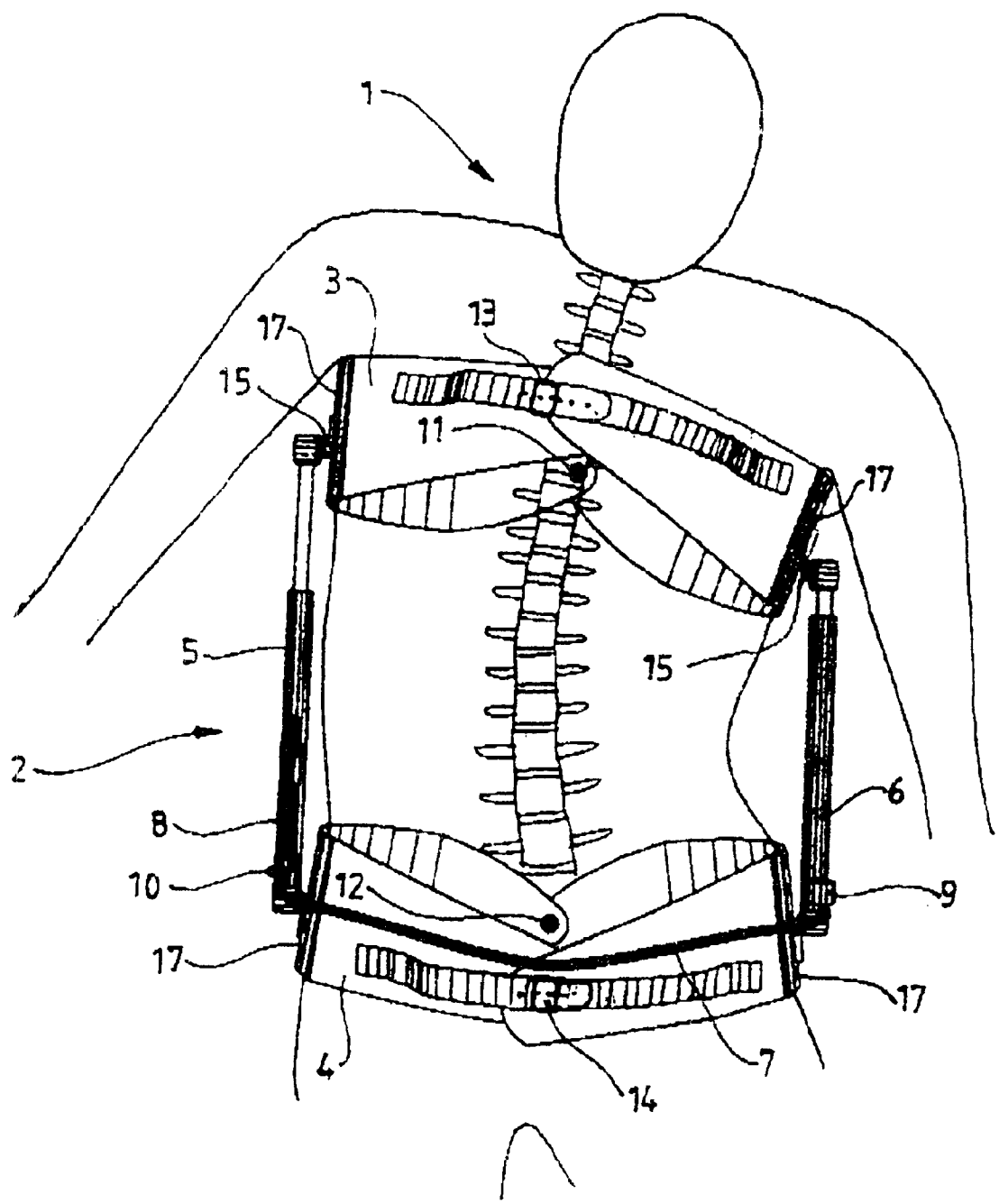
FIG. 2 shows the same as FIG. 1, but here the patient occupies a laterally bent position.
Figure 3:
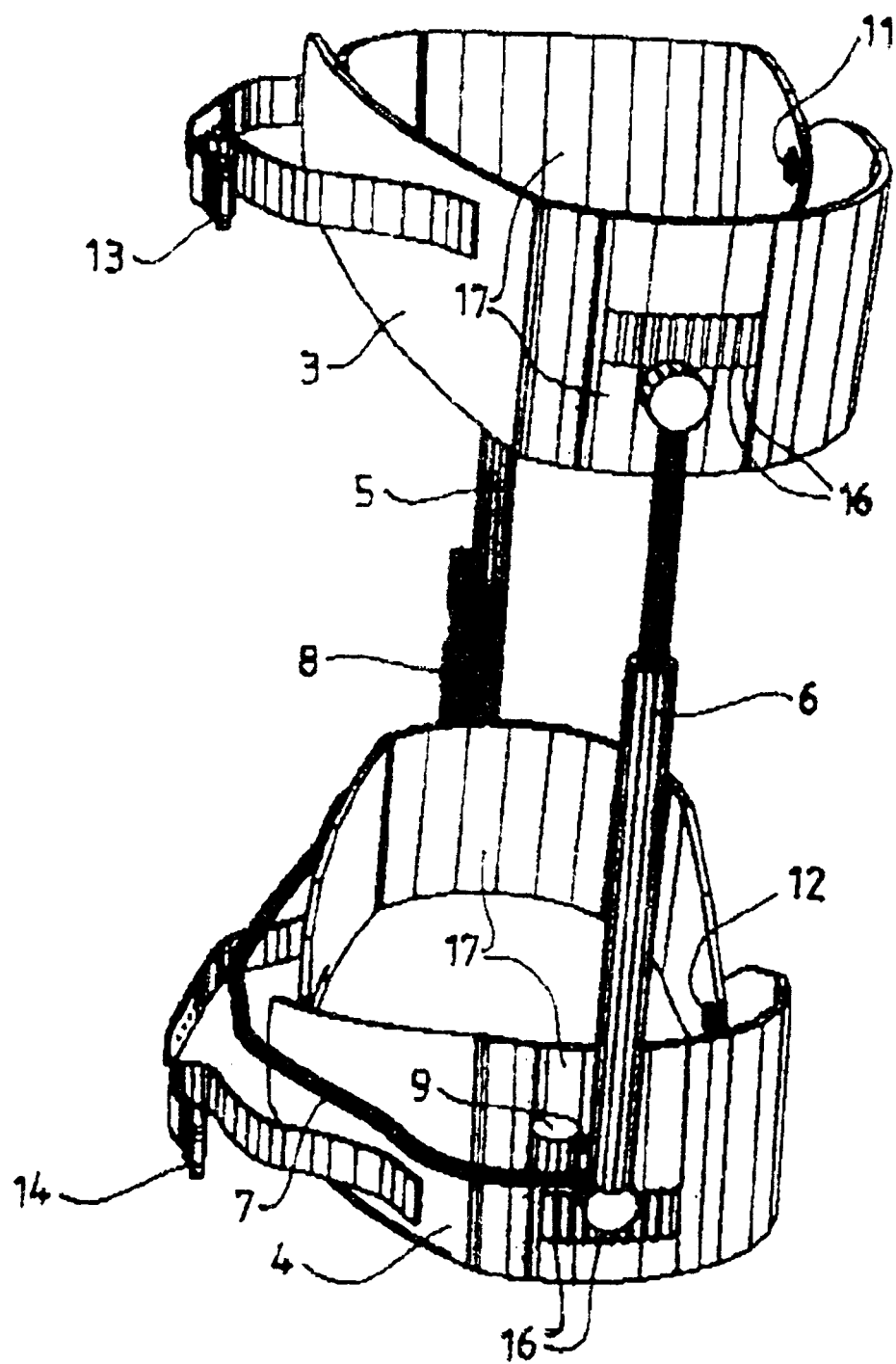
FIG. 3 shows the stretch corset as seen in perspective from one side thereof.

In FIGS. 1 and 2 of the drawings, reference numeral 1 denotes a patient has a stretch corset 2 fastened thereon. This corset comprises a breast belt 3, a hip belt 4, a pneumatic cylinder 5, 6 at either side, communicating freely with each other through a hose 7. A manual pump 8 is connected to cylinder 5 for pumping pressurized air into the cylinders 5 and 6. A manometer 9 has been connected to cylinder 6. A valve 10 is connected to one of the cylinders 5, 6 for letting air out. The breast belt 3 and the hip belt 4 are articulated creating articulation means 11, 12 in the mid-region at the rear side, in order to give a good adaption and mobility for the patient and has, at the front side, a buckle device 13, 14.

In each end thereof, the pneumatic cylinders 5, 6 are each equipped with a hook 15 engaging into a hole 16 of a horizontal row of holes in a rigid portion 17 at each and every side of of the breast belt 3 and the hip belt 4 and, thus, forming two adjustable connections between the breast belt 3 and the hip belt 4.

The patient may well fasten on the stretch corset 2 and inflate the same by means of the manual pump 8, so that the spine is subjected to an adequate tensile force. If the latter has become too large, air may be let out through the valve 10. With the stretch corset fastened on and inflated, the patient may bend and twist freely in all directions, because the pneumatic cylinders 5, 6 communicate and adapted themselves automatically to the movements.

Figure 4:
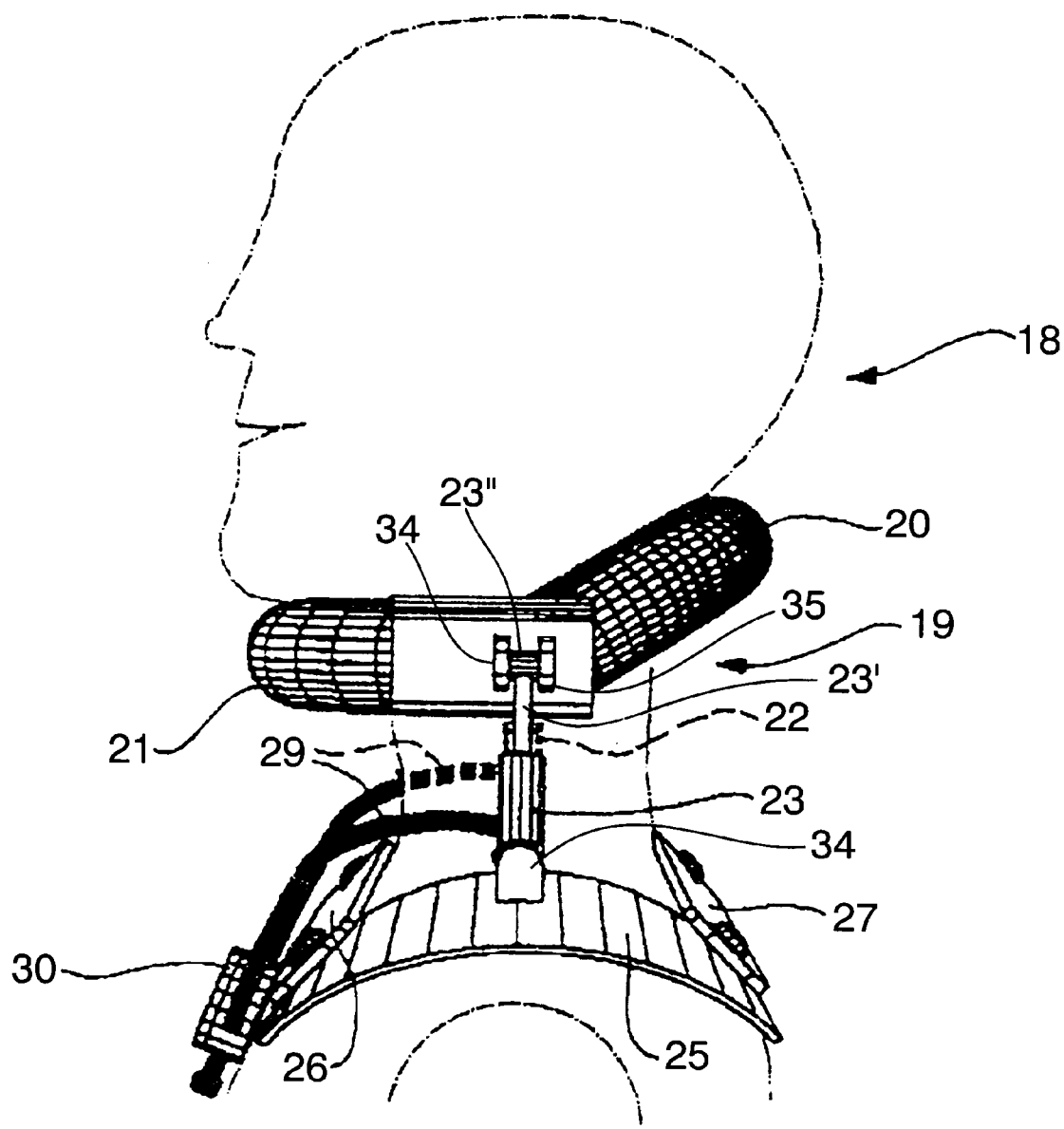
FIG. 4 shows a neck stretcher as seen in a side elevational view, fastened on a patient.
Figure 5:
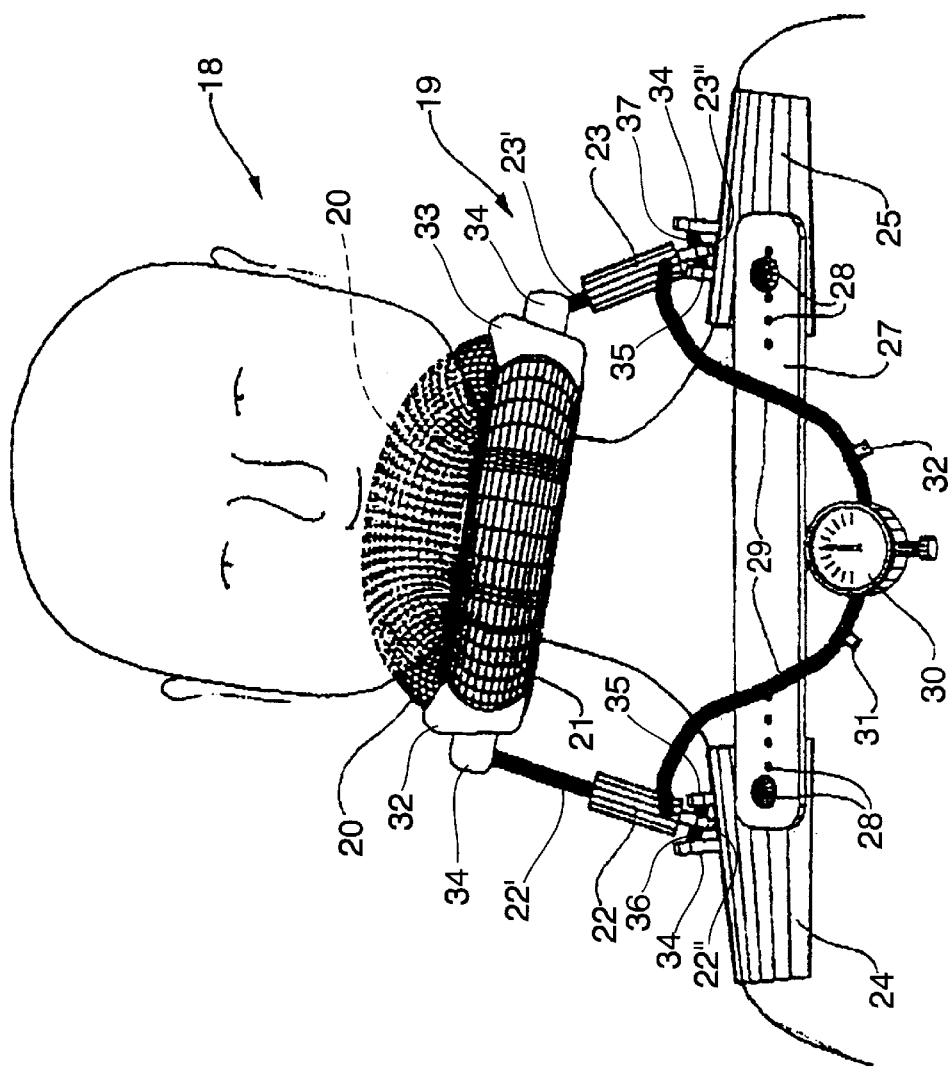
FIG. 5 shows in a front view the same as FIG. 4, but here the patient has bent the head laterally.

In FIGS. 4 and 5 of the drawings, reference numeral 18 denotes a patient having a neck stretcher 19 fastened thereon. This stretcher comprises a neck support 20 which, in front, is connected to a chin support 21; Together the supports 20,21 form a head support. The head support 20, 21 is, at either side thereof, through a pneumatic cylinder 22, 23 movably connected to a yoke consisting of two shoulder supports 24, 25, a breast piece 26 and a back piece 27. The shoulder supports 24, 25 are adjustably (28) connected to the breast piece 26 and the back piece 27, so that the yoke 24, 25, 26, 27 may adjust itself to patients individually. The pneumatic cylinders 22, 23 communicate freely with each other through a hose 29 into which a manometer 30 is inserted. The cylinders 22, 23 may be inflated by means of an ordinary manual pump through a valve 31 within the hose 29. Another valve 32 in the hose 29 is adapted to let out air.

The combined chin and neck support is applied or installed on the user by removing the chin support 21 from the remainder of the neck structure (reference numerals 20, 22, 23, 24 and 25 in FIG. 5) at the axial ends of the chin support. At each side of the stretcher structure is a carrier 32 and 33, respectively, designed to interconnect the free outer ends of the chin support 21 and neck support 20 and also to carry a pair of bearing ears 34 and 35. Each of the piston rods 22' and 23' of the pneumatic cylinders 22 and 23, respectively, includes an attachment means formed with a thickened end piece 22" and 23", each of which is positioned between a pair of bearing ears 34 and 35. An articulated connection is established at each pneumatic cylinder 22 and 23 by means of pivot 36 and 37, respectively, as shown clearly in FIGS. 4 and 5.

The head support 20, 21 is, in a way not illustrated, adapted to be divided. The patient may himself/herself fasten the neck stretcher 19 on and then pump it up so that it becomes adequately tensioned. If the tensioning has become too large, air may be let out through the valve 32. With the neck stretcher fastened on and pumped up, the patient may bend and twist the head freely in all positions, because the pneumatic cylinders 22,23 communicate and adjust themselves automatically to the movements.

Of course, it would be possible to use hydraulic cylinders in lieu of pneumatic ones, but such a solution seems to be less favorable.

What is claimed is:

1. A device for exerting force for stretching out the neck of a patient, comprising:
   a top brace having a neck support adapted to be positioned around the neck and a chin support adapted to be positioned under the chin of a patient;
   a bottom brace adapted to be positioned on the opposed shoulders of a patient;
   a first and second fluid containing cylinder, each cylinder having a lower portion and a telescopically extending upper portion, the cylinders having attachment means thereon and wherein the top and bottom brace are attached to the first and second cylinders through said attachment means attached to said bottom brace, the first and second cylinders adapted to be positioned on opposite sides of the patient's neck, the fluid within said cylinders being compressive and under compression providing a constant force urging said top brace under the patient's chin away from said bottom brace adapted to be positioned on the patient's shoulders to stretch the patient's neck; and
   said neck support and said chin support being directly connected to each other, said neck support forming an obtuse angle with said chin support.

2. A device for exerting force for stretching out the neck of a patient as set forth in claim 1 wherein said first and second fluid containing cylinders are formed of piston cylinders, each said cylinder has an internal cavity therein, said cavities being divided by the piston into a chamber below the piston and a chamber above the piston, in the latter chamber the piston moves and at least the chambers of both cylinders below the pistons being freely connected by means of an open-ended hose.

3. A neck stretching device adapted to stretch out the neck of a patient, comprising:
   a top brace including an upwardly sloping neck support adapted to be positioned around the neck and a substantially horizontal chin support adapted to be positioned under the chin of the patient;
   a bottom brace adapted to be positioned on the opposed shoulders of the patient;
   a first and second pressurized fluid operated cylinders, each cylinder having a lower portion and a telescopically extending upper portion, the cylinders at each axial end thereof having attachment means thereon and said first cylinder upper portion being attached to said top brace through said attachment means, forming an articulated connection therewith, said first cylinder lower portion being attached to said bottom brace through said attachment means, forming an articulated connection therewith, said second cylinder upper and lower portions being articulatedly attached to the top and bottom braces, respectively, in exactly the same manner as the first cylinder upper and lower portions, respectively, said first and second cylinders being adapted to be positioned on opposite sides of the patient's neck, thus forcing said top brace under the patient's chin away from the bottom brace adapted to be positioned on the patient's shoulders to intentionally stretch the patient's neck; and
   said first and second cylinders, by means of a hollow member having a through-going bore, being in fluid communication with each other, said neck support and said chin support being interconnected at each side of the patient's head, said neck support forming an obtuse angle (y) with the chin support.

* * * * *

UNITED STATES PATENT AND TRADEMARK OFFICE
CERTIFICATE OF CORRECTION

PATENT NO. : 6,210,354 B1
DATED : April 3, 2001
INVENTOR(S) : Svein Ousdal

It is certified that error appears in the above-identified patent and that said Letters Patent is hereby corrected as shown below:

<u>Claim,</u>
<u>Claim 1,</u>
Line 14, delete "attached to said bottom brace".

Signed and Sealed this

Sixth Day of November, 2001

*Attest:*

NICHOLAS P. GODICI
*Attesting Officer*     *Acting Director of the United States Patent and Trademark Office*